United States Patent
Hu et al.

(10) Patent No.: US 11,696,705 B2
(45) Date of Patent: Jul. 11, 2023

(54) SITTING POSTURE MEASURING DEVICE, INTELLIGENT CUSHION AND INTELLIGENT SEAT

(71) Applicant: SHENZHEN DARMA TECHNOLOGY CO., LTD., Shenzhen (CN)

(72) Inventors: Junhao Hu, Shenzhen (CN); Chao Yang, Shenzhen (CN)

(73) Assignee: SHENZHEN DARMA TECHNOLOGY CO. LTD., Shenzhen (CN)

( * ) Notice: Subject to any disclaimer, the term of this patent is extended or adjusted under 35 U.S.C. 154(b) by 921 days.

(21) Appl. No.: 16/088,074

(22) PCT Filed: Feb. 14, 2017

(86) PCT No.: PCT/CN2017/073526
§ 371 (c)(1),
(2) Date: Jul. 2, 2020

(87) PCT Pub. No.: WO2017/161977
PCT Pub. Date: Sep. 28, 2017

(65) Prior Publication Data
US 2020/0405193 A1    Dec. 31, 2020

(30) Foreign Application Priority Data
Mar. 25, 2016 (CN) .......................... 201610179615.4

(51) Int. Cl.
*A61B 5/11*    (2006.01)
*A61B 5/00*    (2006.01)

(52) U.S. Cl.
CPC .......... *A61B 5/1116* (2013.01); *A61B 5/6891* (2013.01)

(58) Field of Classification Search
CPC .. A47C 3/16; A47C 7/02; A47C 7/021; A47C 7/0213; A47C 27/14; A47C 31/00;
(Continued)

(56) References Cited

U.S. PATENT DOCUMENTS

| | | | |
|---|---|---|---|
| 6,852,086 B2 | 2/2005 | Atlas et al. | |
| 2009/0106905 A1* | 4/2009 | Ochi ................... | A47C 31/123 177/144 |
| 2015/0038881 A1 | 2/2015 | Gokhale et al. | |

FOREIGN PATENT DOCUMENTS

| | | |
|---|---|---|
| CN | 102846051 A | 1/2013 |
| CN | 103027526 A | 4/2013 |

(Continued)

OTHER PUBLICATIONS

Machine translation of CN104905584A (Year: 2015).*

*Primary Examiner* — David J. McCrosky
(74) *Attorney, Agent, or Firm* — Cheng-Ju Chiang

(57) ABSTRACT

A posture measuring device, an intelligent cushion and an intelligent seat are disclosed. The sitting posture measuring device comprises two fiber optic sensors; a signal processing unit electrically connected to the two fiber optic sensors respectively; and a power supply unit electrically connected to the signal processing unit. The sitting posture measuring device further comprises a prompting unit and/or a wireless communications unit electrically connected to the signal processing unit. The two fiber optic sensors are configured from left to right or from front to back. The fiber optic sensors detect changes in optical signals generated from changes in surface pressure on the sensors, and the signal processing unit analyzes a posture of a user on the basis of changes in optical signals generated from changes in surface pressure on the sensors.

17 Claims, 2 Drawing Sheets

(58) Field of Classification Search
CPC ..... A47C 31/12; A47C 31/123; A47C 31/126; A61B 5/1116; A61B 5/6891; A61B 2562/0266; A61B 5/1114
See application file for complete search history.

(56) References Cited

FOREIGN PATENT DOCUMENTS

| | | |
|---|---|---|
| CN | 104154980 A | 11/2014 |
| CN | 204256912 U | 4/2015 |
| CN | 104905584 A | 9/2015 |
| CN | 105877756 A | 8/2016 |
| CN | 206007252 U | 3/2017 |

\* cited by examiner

SITTING POSTURE MEASURING DEVICE, INTELLIGENT CUSHION AND INTELLIGENT SEAT

CROSS REFERENCE TO RELATED APPLICATIONS

The present application is a 35 U.S.C. § 371 National Phase conversion of International (PCT) Patent Application No. PCT/CN2017/073526, filed on Feb. 14, 2017, which claims priority of Chinese Patent Application No. 201610179615.4, filed on Mar. 25, 2016, the disclosure of which is incorporated by reference herein. The PCT International Patent Application was filed and published in Chinese.

TECHNICAL FIELD

The present invention relates to an intelligent seat, and especially to a sitting posture measuring device, an intelligent cushion and an intelligent seat.

BACKGROUND

A good posture can help people improve their work and study efficiency and relieve tiredness. Long periods of incorrect posture will increase the pressure on bones and muscles and make people feel tired or their limbs numb, and it is easy to cause myopia, hunchback, neck and shoulder pain, lumbar muscle strain, low back pain and so on. Especially for teenagers whose bones are at the developmental stage, prolonged incorrect posture will greatly affect physical development.

A good posture mainly depends on a good habit of people. The market can supply equipments for reminding a long-time sitting. Additionally, China Pat. No. ZL201110178636.1 disclosed a seat with a posture detecting device therein, according to value changes of sensors fixed under the four feet of the seat, the change of body gravity center is analyzed, and thus a posture can be determined. However, the accuracy of this seat is low, and it is not suitable for those seats without feet.

SUMMARY

Technical Problems

An object of the present invention is to provide a posture measuring device, an intelligent cushion and an intelligent seat, to solve the problem of the previous posture measuring device being not suitable for those seats without feet.

Technical Solution

As a first aspect of the present invention, a posture measuring device is provided. The posture measuring device comprises two fiber optic sensors, a signal processing unit electrically connected to the two fiber optic sensors respectively, and a power supply unit electrically connected to the signal processing unit. The posture measuring device further comprises a prompting unit and/or a wireless communications unit electrically connected to the signal processing unit. The two fiber optic sensors are arranged side by side or parallel arranged in front and rear. The fiber optic sensors detect changes in optical signals generated from changes in applied pressures on the sensors, and the signal processing unit analyzes a posture of a user on the basis of changes in optical signals generated from changes detected by the fiber optic sensors in applied pressures on the sensors.

Further, the fiber optic sensor is a fiber optic pressure sensor in a planar shape.

Further, the fiber optic pressure sensor is rectangular or square.

Further, the optical signal is light intensity, wavelength, modulation frequency or phase.

Further, the signal processing unit comprises an opto-electronic conversion circuit, a signal amplification and filter circuit, MCU (Microcontroller Unit), a light source drive circuit and a light source, which are electrically connected in sequence; the opto-electronic conversion circuit and the light source are respectively connected with the fiber optic sensors via fiber optic connectors; MCU is connected with the power supply unit, the prompting unit, and the wireless communications unit respectively.

Further, the posture measuring device comprises a grid stress element. When the two fiber optic sensors are arranged side by side, the grid stress element is placed on a rear side or a front side of an upper surface connected by the two fiber optic sensors side by side; when the two fiber optic sensors are parallel arranged in front and rear, the grid stress element is placed on a left side or a right side of the upper surface connected by the two fiber optic sensors in front and rear.

Further, the grid stress element is a panel with grid projections or a mesh filter.

Further, the posture measuring device comprises another two fiber optic sensors, whereby four fiber optic sensors are respectively arranged in a left front side, a right front side, a left rear side, and a right rear side; and all the four fiber optic sensors are electrically connected with the signal processing unit.

As a second aspect of the present invention, an intelligent cushion is provided. The intelligent cushion comprises a cushion body and the posture measuring device disposed in the cushion body, and then the above described posture measuring device is adopted.

As a third aspect of the present invention, an intelligent seat is provided. The intelligent seat comprises a seat body and a posture measuring device disposed in the seat body, and then the above described posture measuring device is adopted.

Advantages

In the present invention, the posture measuring device has two fiber optic sensors arranged side by side, in such way to determine a user in a posture leaning left or leaning right; alternatively, the posture measuring device has two fiber optic sensors parallel arranged in front and rear, in such way to determine a user in a posture leaning forward or leaning backward. Further alternatively, the posture measuring device comprises two fiber optic sensors side by side and the grid stress element placed on the front side or rear side of the same; or, the posture measuring device comprises two fiber optic sensors parallel arranged in front and rear and the grid stress element placed on the left side or right side of the same; in such way to determine a user in a posture learning forward, leaning backward, leaning left or leaning right. Moreover alternatively, the posture measuring device comprises four fiber optic sensors respectively arranged in a left front side, a right front side, a left rear side, and a right rear side, in such way to determine a user in a posture learning toward left front direction, leaning toward right front direction, learning toward left rear direction, or leaning toward right rear direction.

Because of the high sensitivity of the fiber optic sensors, a micro change in applied pressure can be measured; and because of the fiber optic pressure sensor in a planar shape, micro changes in pressure applied on any position can be captured; thereby, the measurements of posture are more accurate. Additionally, the posture measuring device has good design performance, low cost, good portability and wide application, and can be conveniently imbedded in seats, sofas, and cushions, so it can also apply to seats without feet.

DETAILED DESCRIPTION

The objects, features and advantages of the invention will become more apparent from the following detailed description of the embodiments thereof when taken in conjunction with the accompanying drawings. It is understood that, the detailed description of the embodiments given below, serve to explain the principles of the invention, but is not intended to limit the present invention to these embodiments.

The following description of certain embodiments is used to illustrate the features of the present invention.

First Embodiment

Figure 1:
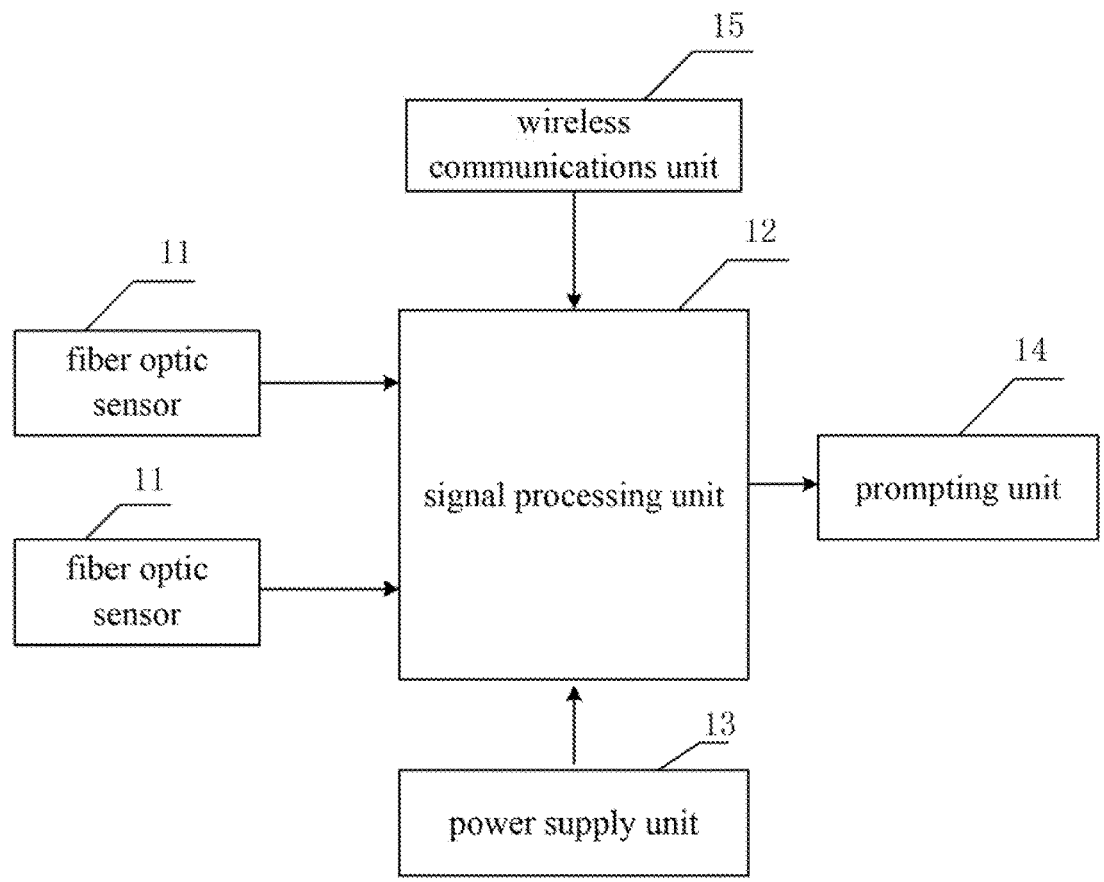
FIG. 1 illustrates a block schematic diagram of a posture measuring device in accordance with a first embodiment of the present invention.

Referring to FIG. 1, a posture measuring device in accordance with the first embodiment of the present invention, comprises two fiber optic sensors 11, a signal processing unit 12 electrically connected with the two fiber optic sensors 11 respectively, and a power supply unit 13 electrically connected with the signal processing unit 12. The posture measuring device in accordance with the first embodiment of the present invention further comprises a prompting unit 14 and/or a wireless communications unit 15 electrically connected with the signal processing unit 12 respectively.

The fiber optic sensors 11 in accordance with the first embodiment of the present invention are fiber optic pressure sensors in planar shape and in appearance similar to mouse pad. And especially, the fiber optic pressure sensors are rectangular or square. The two fiber optic sensors 11 are arranged side by side, or parallel arranged in front and rear respectively. The fiber optic sensors 11 detect changes in optical signals generated from changes in pressure applied on the surfaces of the sensors. Because of the unique correspondence between the applied pressure and the optical signal, that is, when the applied pressure is increased or decreased, the optical signal through the fiber optic sensors changes accordingly, therefore, the changes in applied pressure can be analyzed according to the changes in optical signals. The fiber optic sensor has so high sensitivity that it can measure micro-changes in the applied pressure. The optical signals can be light intensity, wavelength, modulation frequency, phase, etc.

The signal processing unit 12 analyzes a posture of the user based on changes in optical signals generated from changes in pressures applied on the surfaces of the sensors and detected by the two fiber optic sensors 11 side by side or in front or rear. The signal processing unit 12 may comprises an opto-electronic conversion circuit, a signal amplification and filter circuit, MCU, a light source drive circuit and a light source, which are electrically connected in sequence. The opto-electronic conversion circuit and the light source are respectively connected with the fiber optic sensors 11 via fiber optic connectors; and MCU is connected with the power supply unit 13, the prompting unit 14, and the wireless communications unit 15 respectively. When the optical signal is light intensity, and the two fiber optic sensors 11 are arranged side by side, if the user leans to the left, then the applied pressure on the left side will be greater than that on the right side, the optical signal through the left fiber optic sensor 11 will be weaker than that through the right fiber optic sensor 11; while the user leans to the right, then the applied pressure on the right side will be greater than that on the left side, the optical signal through the right fiber optic sensor 11 will be weaker than that through the left fiber optic sensor 11; therefore, by detecting changes in optical signals through the left and right fiber optic sensors 11, the pressure distribution on the two optical fiber sensors 11 can be calculated, and then the posture of the user can be determined. When the optical signal is light intensity, and the two fiber optic sensors 11 are parallel arranged in front and rear, when the user lean forward, then the front applied pressure will be greater than the rear applied pressure, the optical signal through the front fiber optic sensor 11 will be weaker than that through the rear fiber optic sensor 11; while the user lean backward, then the rear applied pressure will be greater than the front applied pressure, the optical signal through the rear fiber optic sensor 11 will be weaker than that through the front fiber optic sensor 11; therefore, by detecting changes in optical signals through the front and rear fiber optic sensors 11, the pressure distribution on the front and rear optical fiber sensors 11 can be calculated, and then a posture of the user can be determined.

The power supply unit 13 is used to supply power to the two fiber optic sensors 11, the prompting unit 14, and the wireless communications unit 15. The power supply unit 13 may be a power adapter connected to the electric supply. The power supply unit 13 may also include a battery charge-discharge management circuit, and a voltage conversion circuit and a storage battery both of which are electrically connected with the battery charge-discharge management circuit. The voltage conversion circuit is electronically with MCU of the signal processing unit 12.

The prompting unit 14 is used to prompt the user under a control of the signal processing unit 12 if the signal processing unit 12 has analyzed that the user has an incorrect posture. The prompting unit 14 may be a buzzer, a LED lamp or a LED display module.

The wireless communications unit 15 is used to transmit the user posture analyzed by the signal processing unit 12 to the user terminal devices. The wireless communications unit 15 may be a WIFI module, a GPRS module, a CDMA module, a GSM module, a Bluetooth module, or a Zigbee module, etc.

The principle of the posture measuring device provided in accordance with the first embodiment of the present invention is as follows:

MCU of the signal processing unit 12 controls the light source drive circuit to drive the light source emitting light wave; the light wave respectively enters into the two fiber optic sensors 11 arranged side by side or parallel arranged in front and rear; changes in optical signals generated from changes in applied pressures on the surface of the sensors are detected by the two fiber optic sensors 11, are further converted into electric signals by the opto-electronic conversion circuit of the signal processing unit 12, and are amplified and filtered by the signal amplification and filter circuit, and then are collected by MCU; MCU can analyze a posture of the user based on the electric signals converted from the changes in optical signals detected by the two fiber optic sensors 11 side by side or in front and rear and generated from changes in applied pressures on the surface of the sensors, transmits the user's posture to the user's terminal device via the wireless communication unit 15, or the prompting unit 14 prompts the user under a control of the signal processing unit 12 if an incorrect posture of the user is detected by the signal processing unit 12.

Second Embodiment

Figure 2:
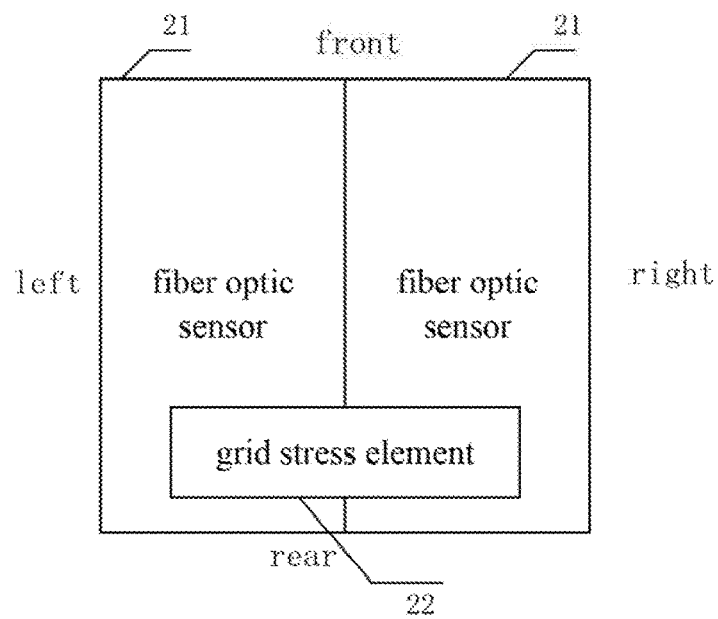
FIG. 2 illustrates a block schematic diagram of the posture measuring device in accordance with a second embodiment of the present invention.
Figure 3:
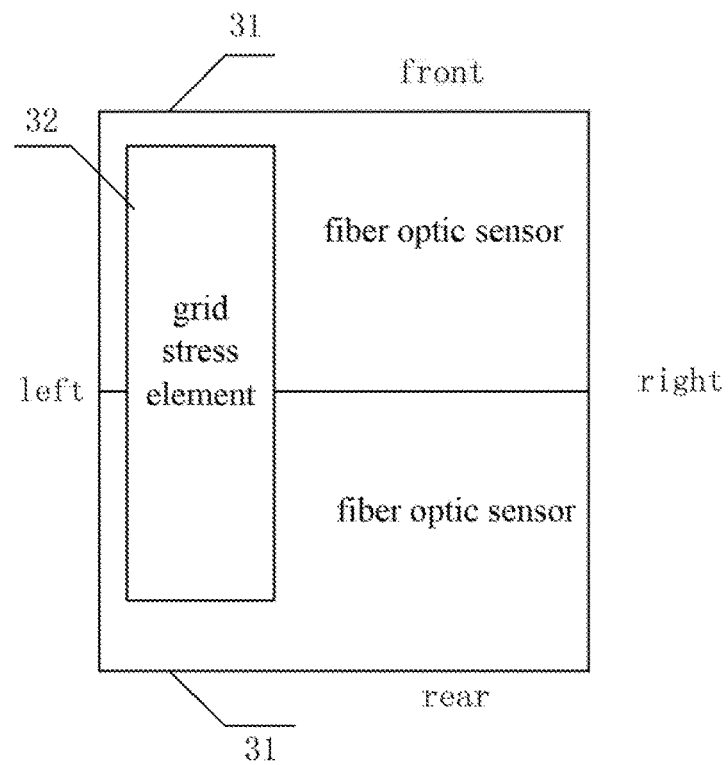
FIG. 3 illustrates a block schematic diagram of another posture measuring device in accordance with the second embodiment of the present invention.

Referring to FIGS. 2 and 3, the difference between the second embodiment and the first embodiment of the present invention is that: the posture measuring device in accordance with the second embodiment further comprises a grid stress element 22. When two fiber optic sensors 21 are arranged side by side, the grid stress element 22 is placed on the front side or at the rear side (FIG. 2 shows at the rear side) of an upper surface connected by the two fiber optic sensors 21 side by side. When two fiber optic sensors 31 are parallel arranged in front and rear, the grid stress element 32 is placed on the left side or the right side (FIG. 3 shows at the left side) of the upper surface connected by the two fiber optic sensors 31 in front and rear.

The grid stress element in accordance with the second embodiment of the present invention, may be a panel with grid projections or a mesh filter, and especially is a mesh of plastic filters. The grid stress element is used to increase the sensitivity of the Optic Fiber in the fiber optic sensor to changes in applied pressure.

The principle of the posture measuring device provided in accordance with the second embodiment of the present invention is as follows:

MCU of the signal processing unit controls the light source drive circuit to drive the light source emitting light wave; the light wave respectively enters into the two fiber optic sensors arranged side by side or arranged in front and rear; changes in optical signals generated from changes in applied pressures on the surface of the sensors are detected by the two fiber optic sensors, are further converted into electric signals by the opto-electronic conversion circuit of the signal processing unit, and are amplified and filtered by the signal amplification and filter circuit, and then are collected by MCU; MCU can analyze a posture of the user based on the electric signals converted from the changes in optical signals detected by the two fiber optic sensors side by side or in front and rear and generated from changes in applied pressures on the surface of the sensors.

When the optical signal is light intensity, and the two fiber optic sensors are arranged side by side, the grid stress element is placed on the rear side of the upper surface connected by the two fiber optic sensors side by side; if the user leans to the left, then the applied pressure on the left side will be greater than that on the right side, and the optical signal through the left fiber optic sensor will be weaker than that through the right fiber optic sensor; while the user leans to the right, then the applied pressure on the right side will be greater than that on the left side, and the optical signal through the right fiber optic sensor will be weaker than that through the left fiber optic sensor; if the user lean forward, because of no grid stress element being set at the front side, applied pressures on the two fiber optic sensors will decrease together and thus optical signals through the two fiber optic sensors will increase together; while the user lean backward, because the grid stress element is placed on the rear side, applied pressures on the two fiber optic sensors will increase together and thus optical signals through the two fiber optic sensors will decrease together. Therefore, by detecting changes in optical signals through the left and right fiber optic sensors, the pressure distribution on the two optical fiber sensors can be calculated, and then a posture of the user such as leaning left, leaning right, leaning forward or leaning backward can be determined. When the grid stress element is placed on the front side of the upper surface connected by the two fiber optic sensors side by side, the principle is similar and is not described here.

When the optical signal is light intensity, and the two fiber optic sensors are parallel arranged in front and rear, the grid stress element is placed on the left side of the upper surface connected by the two fiber optic sensors in front and rear, and if the user lean forward, then the front applied pressure will be greater than the rear applied pressure, and the optical signal through the front fiber optic sensor will be weaker than that through the rear fiber optic sensor; while the user lean backward, then the rear applied pressure will be greater than the front applied pressure, the optical signal through the rear fiber optic sensor will be weaker than that through the front fiber optic sensor; if the user lean left, because the grid stress element is placed on the left side, applied pressures on the two fiber optic sensors will increase together and thus optical signals through the two fiber optic sensors will decrease together; if the user lean right, because of no grid stress element placed on the right side, applied pressures on the two fiber optic sensors will decrease together and thus optical signals through the two fiber optic sensors will increase together. Therefore, by detecting changes in optical signals through the front and fight rear fiber optic sensors, the pressure distribution on the two optical fiber sensors can be calculated, and then the posture of the user such as leaning left, leaning right, leaning forward or leaning backward can be determined. When the grid stress element is placed on the right side of the upper surface connected by the two fiber optic sensors in front and rear, the principle is similar and is not described here.

Finally, the wireless communications unit transmits the posture of the user to a terminal device, or the signal processing unit can control the prompting unit to issue a prompt to the user if the signal processing unit analyzes the user is not sitting correctly.

Third Embodiment

Figure 4:
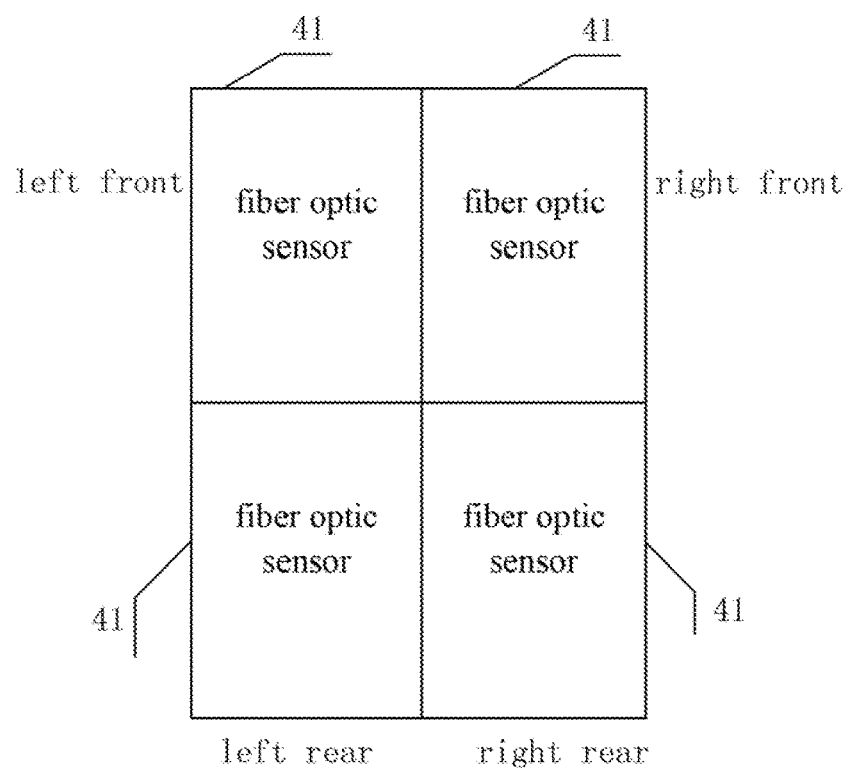
FIG. 4 illustrates a block schematic diagram of the posture measuring device in accordance with a third embodiment of the present invention.

Referring to FIG. 4, the difference between the third embodiment and the first embodiment of the present invention is that: the posture measuring device in accordance with the third embodiment comprises four fiber optic sensors 41. The four fiber optic sensors 41 are respectively arranged in a left front side, a front side, a left rear side, and a right rear side, and are electrically connected with the signal processing unit respectively.

The following will describe the principle of the posture measuring device in accordance with the third embodiment of the present invention of which the optical signal is light intensity, that is:

if the user leans toward left front direction, then the applied pressure on the left front side will be greater than that on other sides, the optical signal through the fiber optic sensor at the left front side will be weaker than that through other fiber optic sensors; while the user leans toward right front direction, then the applied pressure on the right front side will be greater than that on other sides, the optical signal through the fiber optic sensor at the right front side will be weaker than that through other fiber optic sensors; if the user leans toward left rear direction, then the applied pressure on the left rear side will be greater than that on other sides, the optical signal through the fiber optic sensor at the left rear side will be weaker than that through other fiber optic sensors; while the user leans toward right rear direction, then the applied pressure on the right rear side will be greater than that on other sides, the optical signal through the fiber optic sensor at the right rear side will be weaker than that through other fiber optic sensors. Therefore, after the signal processing unit detects changes in optical signals through the four fiber optic sensors respectively at the left front, right front, left rear and right rear sides, pressure distribution on the four optical fiber sensors can be calculated, and then a posture of the user can be determined.

Fourth Embodiment

An intelligent cushion is provided in accordance with the fourth embodiment of the present invention. The intelligent cushion comprises a cushion body and the posture measuring device disposed in the cushion body. The posture measuring device can be any one provided in the first, second or third embodiments of the present invention.

Fifth Embodiment

An intelligent seat is provided in accordance with the fifth embodiment of the present invention. The intelligent seat comprises a seat body and the posture measuring device disposed in the seat body. The posture measuring device can be any one provided in the first, second or third embodiments of the present invention. The intelligent seat provided by the fifth embodiment of the invention includes an intelligent chair, an intelligent sofa, and the like.

In the present invention, the posture measuring device has two fiber optic sensors arranged side by side, in such way to determine a user in a posture leaning left or leaning right; alternatively, the posture measuring device has two fiber optic sensors parallel arranged in front and rear, in such way to determine a user in a posture leaning forward or leaning backward. Further alternatively, the posture measuring device comprises two fiber optic sensors side by side and the grid stress element placed on the front side or rear side of the same; or, the posture measuring device comprises two fiber optic sensors parallel arranged in front and rear and the grid stress element placed on the left side or right side of the same; in such way to determine a user in a posture learning forward, leaning backward, leaning left or leaning right. Moreover alternatively, the posture measuring device comprises four fiber optic sensors respectively arranged in a left front side, a right front side, a left rear side, and a right rear side, in such way to determine a user in a posture learning toward left front direction, leaning toward right front direction, learning toward left rear direction, or leaning toward right rear direction.

Because of the high sensitivity of the fiber optic sensors, a micro change in applied pressure can be measured; and because of the fiber optic pressure sensor in a planar shape, micro changes in pressure applied on any position can be captured; thereby, the measurements of posture are more accurate. Additionally, the posture measuring device has good design performance, low cost, good portability and wide application, and can be conveniently imbedded in seats, sofas, and cushions, so it can also apply to seats without feet.

While the above illustrated and described are only preferable embodiments of the present invention but not used to limit the invention. Any modifications, substitutions, and changes etc. without departing from the spirit of the invention should be included within the scope of this invention.

What is claimed is:

1. A posture measuring device, comprising:
   two fiber optic;
   a signal processing unit electrically connected to the two fiber optic sensors respectively;
   a power supply unit electrically connected to the signal processing unit;
   a prompting unit and/or a wireless communications unit electrically connected to the signal processing unit; and
   a grid stress element;
   wherein the two fiber optic sensors are arranged side by side or parallel arranged in front and rear; the fiber optic sensors detect changes in optical signals generated from changes in applied pressures on the sensors, the signal processing unit analyzes a posture of a user on the basis of changes in optical signals generated from changes detected by the fiber optic sensors in applied pressures on the sensors; when the two fiber optic sensors are arranged side by side, the grid stress element is placed on a rear side or a front side of an upper surface connected by the two fiber optic sensors side by side; when the two fiber optic sensors are parallel arranged in front and rear, the grid stress element is placed on a left side or a right side of the upper surface connected by the two fiber optic sensors in front and rear.

2. The posture measuring device of claim 1, wherein the fiber optic sensor is a fiber optic pressure sensor in a planar shape.

3. The posture measuring device of claim 2, wherein the fiber optic pressure sensor is rectangular or square.

4. The posture measuring device of claim 1, wherein the optical signal is light intensity, wavelength, modulation frequency or phase.

5. The posture measuring device of claim 1, wherein the signal processing unit comprises an opto-electronic conversion circuit, a signal amplification and filter circuit, MCU (Microcontroller Unit), a light source drive circuit and a light source, all of which are electrically connected in sequence; the opto-electronic conversion circuit and the light source are respectively connected with the fiber optic sensors via fiber optic connectors; MCU is connected with the power supply unit, the prompting unit, and the wireless communications unit respectively.

6. The posture measuring device of claim 1, wherein the grid stress element is a panel with grid projections or a mesh filter.

7. The posture measuring device of claim 1, wherein the posture measuring device comprises another two fiber optic sensors, whereby four fiber optic sensors are respectively arranged in a left front side, a right front side, a left rear side, and a right rear side; and all the four fiber optic sensors are electrically connected with the signal processing unit.

8. An intelligent cushion, compressing:
a cushion body; and
a posture measuring device disposed in the cushion body;
the posture measuring device comprising:
  two fiber optic sensors;
  a signal processing unit electrically connected to the two fiber optic sensors respectively;
  a power supply unit electrically connected to the signal processing unit;
  a prompting unit and/or a wireless communications unit electrically connected to the signal processing unit; and
  a grid stress element;
wherein the two fiber optic sensors are arranged side by side or parallel arranged in front and rear; the fiber optic sensors detect changes in optical signals generated from changes in applied pressures on the sensors, the signal processing unit analyzes a posture of a user on the basis of changes in optical signals generated from changes detected by the fiber optic sensors in applied pressures on the sensors; when the two fiber optic sensors are arranged side by side, the grid stress element is placed on a rear side or a front side of an upper surface connected by the two fiber optic sensors side by side; when the two fiber optic sensors are parallel arranged in front and rear, the grid stress element is placed on a left side or a right side of the upper surface connected by the two fiber optic sensors in front and rear.

9. The intelligent cushion of claim 8, wherein the fiber optic sensor is a fiber optic pressure sensor in a planar shape; and the fiber optic pressure sensor is rectangular or square; the optical signal is light intensity, wavelength, modulation frequency or phase.

10. The intelligent cushion of claim 8, wherein the signal processing unit comprises an opto-electronic conversion circuit, a signal amplification and filter circuit, MCU (Microcontroller Unit), a light source drive circuit and a light source, all of which are electrically connected in sequence; the opto-electronic conversion circuit and the light source are respectively connected with the fiber optic sensors via fiber optic connectors; MCU is connected with the power supply unit, the prompting unit, and the wireless communications unit respectively.

11. The intelligent cushion of claim 8, wherein the grid stress element is a panel with grid projections or a mesh filter.

12. The intelligent cushion of claim 8, wherein the posture measuring device comprises another two fiber optic sensors, whereby four fiber optic sensors are respectively arranged in a left front side, a right front side, a left rear side, and a right rear side; and all the four fiber optic sensors are electrically connected with the signal processing unit.

13. An intelligent seat, comprising:
a seat body; and
a posture measuring device disposed in the seat body;
the posture measuring device comprising:
  two fiber optic sensors;
  a signal processing unit electrically connected to the two fiber optic sensors respectively;
  a power supply unit electrically connected to the signal processing unit;
  a prompting unit and/or a wireless communications unit electrically connected to the signal processing unit; and
  a grid stress element;
wherein the two fiber optic sensors are arranged side by side or parallel arranged in front and rear; the fiber optic sensors detect changes in optical signals generated from changes in applied pressures on the sensors, the signal processing unit analyzes a posture of a user on the basis of changes in optical signals generated from changes detected by the fiber optic sensors in applied pressures on the sensors; when the two fiber optic sensors are arranged side by side, the grid stress element is placed on a rear side or a front side of an upper surface connected by the two fiber optic sensors side by side; when the two fiber optic sensors are parallel arranged in front and rear, the grid stress element is placed on a left side or a right side of the upper surface connected by the two fiber optic sensors in front and rear.

14. The intelligent seat of claim 13, wherein the fiber optic sensor is a fiber optic pressure sensor in a planar shape; and the fiber optic pressure sensor is rectangular or square; the optical signal is light intensity, wavelength, modulation frequency or phase.

15. The intelligent seat of claim 13, wherein the signal processing unit comprises an opto-electronic conversion circuit, a signal amplification and filter circuit, MCU (Microcontroller Unit), a light source drive circuit and a light source, all of which are electrically connected in sequence; the opto-electronic conversion circuit and the light source are respectively connected with the fiber optic sensors via fiber optic connectors; MCU is connected with the power supply unit, the prompting unit, and the wireless communications unit respectively.

16. The intelligent seat of claim 13, wherein the grid stress element is a panel with grid projections or a mesh filter.

17. The intelligent seat of claim 13, wherein the posture measuring device comprises another two fiber optic sensors, whereby four fiber optic sensors are respectively arranged in a left front side, a right front side, a left rear side, and a right rear side; and all the four fiber optic sensors are electrically connected with the signal processing unit.

* * * * *